United States Patent [19]

Kaneko et al.

[11] Patent Number: 5,471,004
[45] Date of Patent: Nov. 28, 1995

[54] PROCESS FOR PRODUCING α,β-UNSATURATED ALDEHYDES

[75] Inventors: Tatsuhiko Kaneko, Shimamoto; Noritaka Kuroda, Toyono; Kenichi Kashiwa, Kobe, all of Japan

[73] Assignee: Takeda Chemical Industries, Ltd., Osaka, Japan

[21] Appl. No.: 260,233

[22] Filed: Jun. 14, 1994

[30] Foreign Application Priority Data

Jun. 14, 1993 [JP] Japan ................... 5-142135

[51] Int. Cl.[6] ............................................. C07C 45/42
[52] U.S. Cl. ............................................. 568/455; 568/436
[58] Field of Search ........................ 560/262, 241; 568/426, 449, 436, 455

[56] References Cited

U.S. PATENT DOCUMENTS

| | | | |
|---|---|---|---|
| 4,058,566 | 11/1977 | Martan | 568/436 |
| 4,079,182 | 3/1978 | Savins et al. | 568/436 |
| 4,101,564 | 7/1978 | Poist | 568/455 |
| 4,175,204 | 11/1979 | Babler | 560/262 |

FOREIGN PATENT DOCUMENTS 736488  9/1953  United Kingdom .

*Primary Examiner*—Werren B. Lone
*Attorney, Agent, or Firm*—Wenderoth, Lind & Ponack

[57] ABSTRACT

The present invention relates to a process for producing an α,β-unsaturated aldehyde which comprises subjecting an allyl-hexamethylenetetraammonium derivative to hydrolysis in water and an organic solvent homogeneously immiscible with water. The resulting α,β-unsaturated aldehyde is useful as medicaments, flavorings, etc., or as raw materials for their production.

32 Claims, No Drawings

PROCESS FOR PRODUCING α,β-UNSATURATED ALDEHYDES

FIELD OF THE INVENTION

The present invention relates to a process for producing α, β-unsaturated aldehydes useful as medicaments, flavorings, etc., or as raw materials for their production.

BACKGROUND OF THE INVENTION

The following processes have been known for producing α, β-unsaturated aldehydes useful as medicaments, flavorings, etc., or as raw materials for their production.

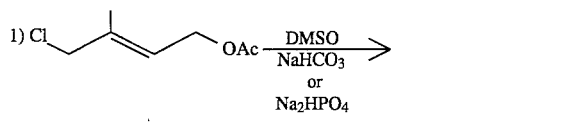

[U.S. Pat. No. 4,175,204; J. Org. Chem. 44, 1716 (1979)]

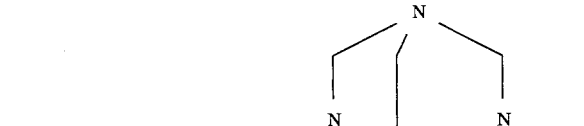

[GB Patent No. 736488 (1955)]

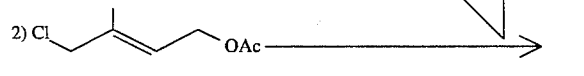

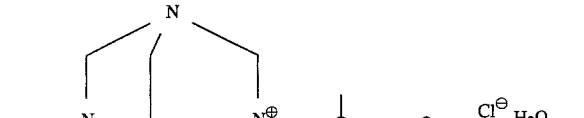

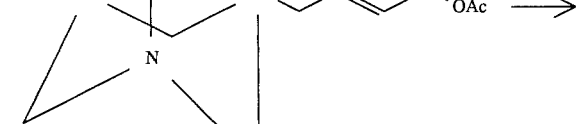

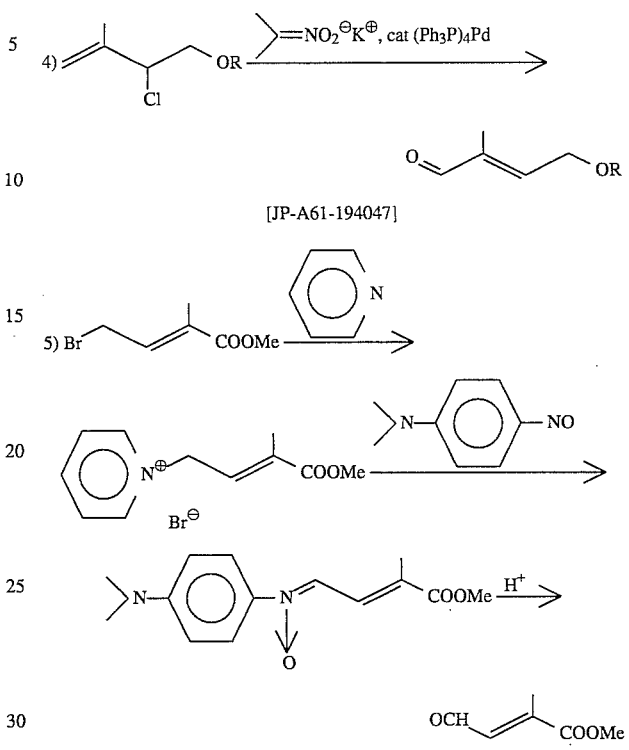

Each of the above processes is problematic. For example, Method No. 1 is environmentally unsuitable because of dimethyl sulfide responsible for the bad smell produced in the reaction. The yield of the Method No.2 is quite low. Method Nos. 3, 4 and 5 involve many reaction steps, require severe reaction conditions or reagents which must be handled with great care, and produce the desired product in low yields.

OBJECTS OF THE INVENTION

The main object of the present invention is to provide a process for readily producing α, β-unsaturated aldehydes in high yield and purity using inexpensive raw materials.

This object as well as other objects and advantages of the present invention will become apparent to those skilled in the art from the following description.

SUMMARY OF THE INVENTION

The present inventors have intensively studied to achieve the above objects. As a result, it has been found that the above α, β-unsaturated aldehydes can be produced by hydrolyzing, in water and an organic solvent homogeneously immiscible with water, a quaternary ammonium salt composed of hexamethylenetetramine (hereinafter sometimes referred to as hexamine) and an optionally substituted allyl group attached to one nitrogen atom of the hexamine.

In one aspect, the present invention provides a process for producing a compound of the formula (II):

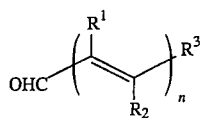

wherein $R^1$ and $R^2$ are each hydrogen or an alkyl group, $R^3$ is hydrogen or an optionally substituted hydrocarbon group, and n is an integer of 1 to 10, which comprises subjecting a compound of the formula (I):

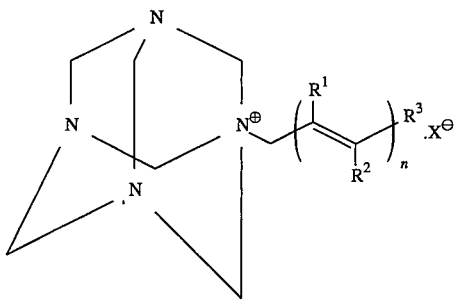

wherein X is halogen and the other symbols are as defined above, to hydrolysis in water and an organic solvent homogeneously immiscible with water.

In another aspect, the present invention provides a process for producing a compound of the formula (II):

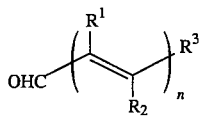

wherein $R^1$ and $R^2$ are each hydrogen or an alkyl group, $R^3$ is hydrogen or an optionally substituted hydrocarbon group, and n is an integer of 1 to 10, which comprises:

reacting a compound of the formula (IV):

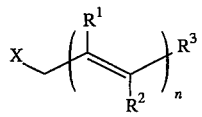

wherein X is halogen and the other symbols are as defined above, with hexamethylenetetramine in water and/or an organic solvent to give a compound of the formula (I):

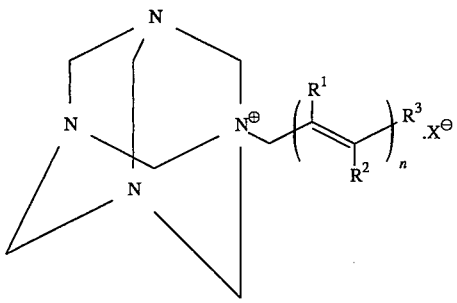

wherein each symbol is as defined above and a compound of the formula (II):

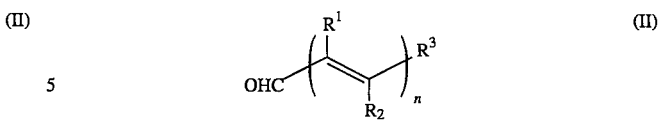

wherein each symbol is as defined above; followed by, if necessary, adding water or organic solvent to the reaction mixture, and then separating the resultant mixture into aqueous and organic layers, and i) subjecting the resultant compound of the formula (I) in the aqueous layer to hydrolysis in the presence of an organic solvent homogeneously immiscible with water, while ii) reacting the resultant compound of the formula (II) in the organic layer with sodium hydrogensulfite to give a compound of the formula (III):

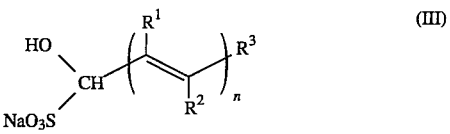

wherein each symbol is as defined above, and reacting the compound of the formula (III) with formaldehyde in water and an organic solvent homogeneously immiscible with water.

Still in another aspect, the present invention provides a method of purifying a compound of the formula (II):

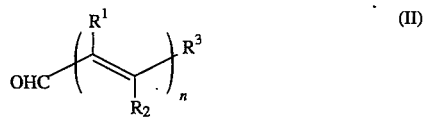

wherein $R^1$ and $R^2$ are each hydrogen or an alkyl group, $R^3$ is hydrogen or an optionally substituted hydrocarbon group, and n is an integer of 1 to 10, which comprises:

reacting a compound of the formula (II) with sodium hydrogensulfite to give the compound of the formula (III):

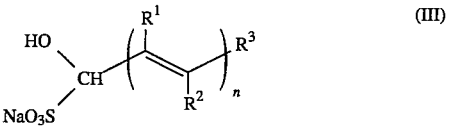

wherein each symbol is as defined above, and reacting the compound of the formula (III) with formaldehyde in water and an organic solvent homogeneously immiscible with water.

DETAILED DESCRIPTION OF THE INVENTION

The alkyl group represented by $R^1$ or $R^2$ includes, for example, straight-chain or branched alkyl groups, preferably straight-chain or branched alkyl groups having 1 to 6 carbon atoms. Examples of the alkyl group include methyl, ethyl, propyl, isopropyl, butyl, sec-butyl, tert-butyl, pentyl, hexyl, etc. Preferred examples are straight-chain or branched alkyl groups having 1 to 3 carbon atoms such as methyl, ethyl, propyl, isopropyl, etc.

The hydrocarbon group of the optionally substituted hydrocarbon group represented by $R^3$ includes, for example, alkyl groups, alkenyl groups, alkynyl groups, aryl groups, aralkyl groups, etc. Preferably, the hydrocarbon group is that having 1 to 20 carbon atoms.

The alkyl group as the above hydrocarbon group includes, for example, the same alkyl groups as those represented by $R^1$. The alkyl group is preferably a straight-chain or branched alkyl group having 1 to 6 carbon atoms.

Preferred examples of the alkenyl group as the above hydrocarbon group include alkenyl groups having 2 to 6 carbon atoms such as vinyl, allyl, 2-butenyl, methylallyl, 3-butenyl, 2-pentenyl, 4-pentenyl, 5-hexenyl, etc.

Preferred examples of the alkynyl group as the above hydrocarbon group include alkynyl groups having 2 to 6 carbon atoms such as ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.

Preferred examples of the aryl group as the above hydrocarbon group include aryl groups having 6 to 10 carbon atoms such as phenyl, 1-naphthyl, 2-naphthyl, etc.

Preferred examples of the aralkyl group as the above hydrocarbon group include aralkyl groups having 7 to 19 carbon atoms such as benzyl, phenethyl, benzhydryl, 1-phenylpropyl, etc.

The substituent of the above substituted hydrocarbon group include, for example, alkoxy groups, acyloxy groups, alkoxycarbonyl groups, a cyano group, an oxo group, a group of the formula:

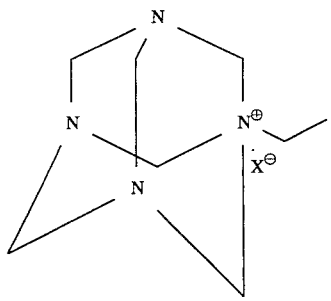

wherein X is halogen. Each of these substituents may have 1 to 3 appropriate substituents.

Examples of the alkoxy groups as the substituent of the hydrocarbon group include $C_{1-4}$ alkoxy groups such as methoxy, ethoxy, propoxy, butoxy, etc.

Preferred examples of the acyloxy groups as the substituent of the hydrocarbon group include acyloxy groups having 1 to 10 carbon atoms such as $C_{1-10}$ alkyl-carbonyloxy groups (e.g., acetoxy, propionyloxy, butyryloxy, etc.), $C_{6-10}$ arylcarbonyloxy groups (e.g., benzoyloxy, naphthoyloxy, etc.), etc.

Examples of the alkoxycarbonyl group as the substituent of the hydrocarbon group include $C_{1-5}$ alkoxy-carbonyl groups such as methoxycarbony, ethoxycarbonyl, propoxycarbonyl, butoxycarbonyl, etc.

When the above hydrocarbon group is substituted, the number of the substituent is preferably 1 to 3.

Examples of the halogen represented by X include chlorine, bromine, fluorine, iodine, etc.

n is preferably an integer of 1 to 5, more preferably 1.

Preferably, $R^1$ is a methyl group. Preferably, $R^2$ is hydrogen. Preferably, $R^3$ is an acetoxymethyl group.

In one aspect of the process of the present invention, the compound (I) subjected to hydrolysis in water and an organic solvent homogeneously immiscible with water to give the compound (II).

Examples of the organic solvent include hydrocarbons (e.g., hexane, toluene, benzene, xylene, etc.), halogenated hydrocarbons (e.g., dichloromethane, 1,2-dichloroethane, chloroform, etc.), ethers (e.g., isopropyl ether, etc), esters (e.g., ethyl acetate, etc.); etc. Preferred examples of the organic solvent are hydrocarbons, halogenated hydrocarbons and ethers, more preferably toluene, dichloromethane and isopropyl ether. The amount of the organic solvent is preferably about 1 to about 3 times (v/v) the amount of the water.

The amount of water to be used is about 0.5 to about 2 liters per mol of the compound (I).

As described above, the solvent used in the hydrolysis comprises water and the above organic solvent. Preferably, the hydrolysis is carried out while maintaining the pH of the solvent to about 4 to about 7. The pH may be adjusted, for example, by using an acid such as acetic acid, sulfuric acid, hydrochloric acid, ion-exchange resin (e.g., acidic resin·Na type), etc. The amount of the acid to be used is preferably about 0.5 to about 3 mol per mol of the compound (I).

The reaction may be continued for about 1 to about 12 hours. The solvent may be separated every several hours, followed by newly adding the solvent for continuing the reaction. These operations may be repeated. For example, the solvent may newly be added about twice every 6 hours. The reaction temperature is room temperature (about 10° C. to 28° C.) to about 100° C., preferably about 60° C. to about 80° C.

After completion of the reaction, the organic layer may be separated, the solvent may be evaporated, and then the residue may be distilled or purified by column chromatography.

The compound (I) used as the starting material in the process can be obtained by reacting a compound of the formula (IV):

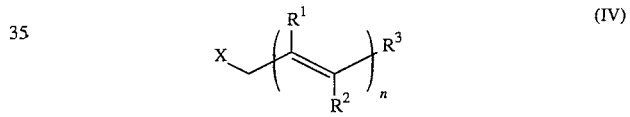

wherein each symbol is as defined above, with hexamine. Normally, the reaction is carried out in water at about 0° C. to about 40° C. to give an aqueous solution of the compound (I). The reaction time is about 3 to about 24 hours. The reaction may be carried out in an organic solvent to obtain the compound (I) in crystal form. In this case, the reaction temperature is about 0° to about 100° C., preferably about 20° C. to about 60° C. Examples of the solvent include halogenated hydrocarbons (e.g., dichloromethane, 1,2-dichloroethane, chloroform, etc.), ethers (e.g., isopropyl ether, tetrahydrofuran, etc.), esters (e.g., ethyl acetate, etc.), amides (e.g., dimethylformamide, etc.), nitriles (e.g., acetonitrile, etc.), alcohols (e.g., methanol, ethanol, etc.), etc. In particular, chloroform, 1,2-dichloromethane and acetonitrile are preferred. The amount of the solvent to be used is preferably about 0.5 to about 2 liters per mol of the compound (IV). The reaction time is about 3 to about 24 hours.

In another aspect of the present invention, to purify the compound (II), the compound (II) containing reactants or impurities is reacted with sodium hydrogensulfite to give the hydrogensulfite adduct the compound (III), which is then reacted with formaldehyde in water and an organic solvent homogeneously immiscible with water to give the compound (II). This method gives a highly purified α,β-unsaturated aldehyde in high yield. In particular, this method is useful for recovery of an α,β-unsaturated aldehyde which is difficult to purify by the above process.

As sodium hydrogensulfite, commercially available 35% aqueous solution thereof may be used as it is or after 1- to 3-fold dilution of the solution. The amount of the sodium hydrogensulfite to be used is preferably about 1 to about 2 mol per mol of the compound (II). The reaction giving the compound (III) is normally carried out in water, and the reaction temperature is preferably about 0° C. to about 50° C.

The reaction between the compound (III) and formaldehyde may be carried out in an organic solvent. Examples of the solvent include halogenated hydrocarbons (e.g., dichloromethane, 1,2-dichloroethane, chloroform, etc.), ethers (e.g., isopropyl ether, etc.), esters (e.g., ethyl acetate, etc.), etc. As the formaldehyde, a commercially available 37% aqueous solution thereof (i.e., formalin) can conveniently be used as it is. The amount of formaldehyde to be used is preferably about 1 to about 2 mol per mol of the compound (II). The reaction temperature is preferably about 0° C. to about 50° C. The reaction time is preferably about 0.5 to about 3 hours.

After completion of the reaction, the reaction mixture is separated, the organic layer is dried over sodium sulfate, and the solvent is evaporated to give the desired $\alpha,\beta$-unsaturated aldehyde.

As described above, according to the present invention, without using special apparatuses or reaction conditions, $\alpha,\beta$-unsaturated aldehydes of the formula (II) can readily be produced in high yield through a few steps using inexpensive raw materials and reagents which can easily be handled in industrial production. The process and method of the present invention can be used even for the production of $\alpha,\beta$-unsaturated aldehydes having a substituent unstable to an acid or alkali. The $\alpha,\beta$-unsaturated aldehydes produced by the invention are useful as medicaments, flavorings, or raw materials for the production thereof.

Further, the method or process of the present invention affords aldehydes in high purity which is difficult to purify by conventional purification techniques such as distillation, chromatography, etc.

The following examples further illustrate the present invention in detail, but are not to be construed to limit the scope thereof.

EXAMPLE 1

1-Acetoxy-4-chloro-3-methyl-2-butene (7.8 g) was added to a suspension of hexamine (6.7 g) and acetonitrile (47 ml), and the mixture was stirred at room temperature for 16 hours. The precipitated crystals were separated by filtration to give crystals (12.5 g) of a quaternary ammonium salt. This salt (7.9 g) was dissolved in water (50 ml), and toluene (100 ml) was added. With stirring at 75° C., acetic acid (1.5 g per addition) was added 30 minutes, 1 hour and 2 hours after the beginning of the reaction. The reaction was stopped 6 hours after the beginning of the reaction. The toluene layer was separated and concentrated, and the resulting residue was purified by column chromatography on silica gel to give 4-acetoxy- 2-methyl-2-buten-1-al (2.6 g, 74%).

EXAMPLE 2

(a) Crude 1-acetoxy-4-chloro-3-methyl-2-butene (194 g, Purity: 83.8%, 1 mol) was added to hexamine (168 g, 1.2 mol)/water (1 liter), and the mixture was stirred at 35° C. for 4 hours and then separated into aqueous and organic layers. 1,2-Dichloroethane (1 liter) was added to the aqueous layer, and the mixture was subjected to reaction at 72° C. for 6 hours while adjusting the pH with 1N sulfuric acid. The 1,2-dichloroethane layer was separated, 1,2-dichloroethane (1 liter) was added to the aqueous layer, and the reaction was carried out again. The 1,2-dichloroethane layers were combined and concentrated. The residue was distilled under reduced pressure to give 4-acetoxy-2-methyl-2-buten-1-al (98 g, 69%). bp.$_{0.2-0.3}$ mmHg: 58°–66° C.

(b) Aqueous 35% sodium hydrogensulfite solution (9 g) and ice-cooled water (100 g) were added to the above organic layer (volume: 50 ml) containing 4-acetoxy-2-methyl-2-buten- 1-al (4.3 g, determined by gas chromatography). The mixture was stirred well, and the aqueous layer was separated. To the aqueous layer was added 1,2-dichloroethane (100 ml). To this mixture was added 37% aqueous formaldehyde solution (10 ml). The resulting mixture was stirred at 30° to 40° C. for 3 hours. The 1,2-dichloroethane layer was separated and concentrated to give 4-acetoxy-2-methyl-2-buten-1-al (3.4 g, Recovery: 79%). Total yield ((a)+(b)): 101.4 g (71.4% from 1-acetoxy-4-chloro-3-methyl-2-butene).

EXAMPLE 3

Cinnamyl chloride (8 g) was added to a suspension of hexamine (7.3 g) in acetonitrile (60 ml), and the mixture was stirred at room temperature for 2 hours. The precipitated crystals were separated by filtration to give a quaternary ammonium salt (14.4 g). This salt (7.3 g) was dissolved in water (70 ml), toluene (70 ml) was added, and the mixture was treated according to the same manner as in Example 1 to give cinnamaldehyde (2.73 g, 83%).

EXAMPLE 4

4-Bromo-1,1-dimethoxy-2-methyl-2-butene (2 g) was added to a solution of hexamine (1.7 g) and water (10 ml), and the mixture was stirred at room temperature for 14 hours. Dowex 50×8 (type H)(3 g) was previously treated with sodium chloride to convert it to type Na. Then isopropyl ether (20 ml) was added to the above reaction mixture, the type Na resin was added, and the mixture was stirred at 70° C. for 6 hours. The isopropyl ether layer was separated, concentrated and purified by column chromatography to give 4,4-dimethoxy-2-methyl- 2-buten-1-al (0.92 g, 64%).

EXAMPLE 5

Geranyl chloride (1 g) was added to a suspension of hexamine (1 g) and dichloromethane (10 ml), and the mixture was stirred at room temperature for 16 hours. The dichloromethane was evaporated, water (10 ml) and isopropyl ether (10 ml) were added to the residue. The mixture was stirred at 70° C. while slowly dropping 1N sulfurinc acid (3 ml) therein. Treatment according the same manner as in Example 1 gave citral (0.62 g, 80%).

EXAMPLE 6

1-Bromo-3-carbomethoxy-2-butene (2 g) was added to a suspension of hexamine (1.7 g) and dichloromethane (10 ml), and the mixture was stirred at room temperature for 16 hours. Then the dichloromethane was evaporated, water (10 ml) and isopropyl ether (10 ml) were added to the residue, acetic acid (1.8 ml) was added, the mixture was stirred at 70° C. for 6 hours and treated according to the same manner as in Example 1 to give 3-carbomethoxy-2-buten-1-al (0.83 g, 65%).

EXAMPLE 7

Methyl 4-bromo-3-methyl-2-butenoate (2 g) was treated according to the same manner as in Example 6 to give methyl 3-formyl-2-butenoate (0.98 g, 77%).

What is claimed is:

1. A process for producing a compound of the formula (II):

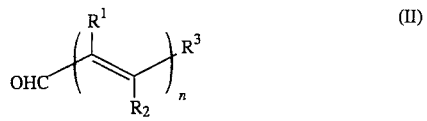

wherein $R^1$ and $R^2$ are each hydrogen or a straight-chain or branched alkyl group having 1 to 6 carbon atoms, $R^3$ is hydrogen or an unsubstituted or substituted hydrocarbon group having 1 to 20 carbon atoms, and n is an integer of 1 to 10, which comprises subjecting a compound of the formula (I):

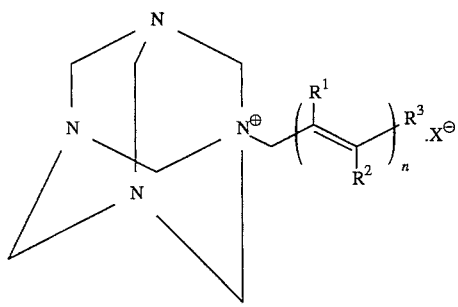

wherein X is halogen and the other symbols are as defined above, to hydrolysis in water and an organic solvent selected from the group consisting of hydrocarbons, halogenated hydrocarbons, ethers and esters.

2. A process according to claim 1, wherein the hydrocarbon group of the unsubstituted or substituted hydrocarbon group represented by $R^3$ is a straight-chain or branched alkyl group having 1 to 6 carbon atoms.

3. A process according to claim 1, wherein the substituent of the substituted hydrocarbon group represented by $R^3$ is $C_{1-4}$ alkoxy group, $C_{1-10}$ acyloxy group, $C_{1-5}$ alkoyxcarbonyl group, cyano group, oxo group or group of the formula:

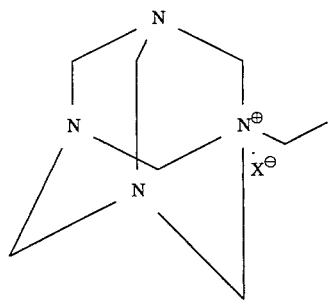

wherein X is halogen.

4. A process according to claim 1, wherein the substituent of the substituted hydrocarbon group represented by $R^3$ is an acyloxy group having 1 to 10 carbon atoms.

5. A process according to claim 1, wherein n is an integer of 1 to 5.

6. A process according to claim 1, wherein $R^1$ is a methyl group, $R^2$ is hydrogen, $R^3$ is an acetoxymethyl group, and n is 1.

7. A process according to claim 1, wherein the amount of the organic solvent is about 1 to about 3 times (v/v) the amount of the water.

8. A process according to claim 1, wherein the amount of the water is about 0.5 to about 2 liters per mol of the compound of the formula (I).

9. A process according to claim 1, wherein the hydrolysis is carried out at a pH of about 4 to about 7.

10. A process according to claim 1, wherein the organic solvent is selected from hydrocarbons, halogenated hydrocarbons and ethers.

11. A process according to claim 1, wherein the hydrolysis is carried out at about 60° to about 80° C.

12. A process for producing a compound of the formula (II):

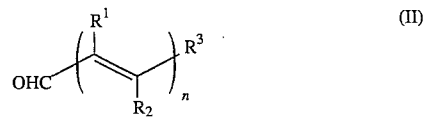

wherein $R^1$ and $R^2$ are each hydrogen or a straight-chain or branched alkyl group having 1 to 6 carbon atoms, $R^3$ is hydrogen or an unsubstituted or substituted hydrocarbon group having 1 to 20 carbon atoms, and n is an integer of 1 to 10, which comprises:

reacting a compound of the formula (IV):

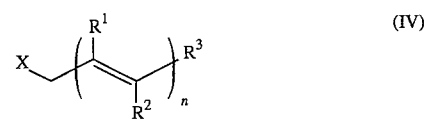

wherein X is halogen and the other symbols are as defined above, with hexamethylenetetramine in a solvent selected from water, an organic solvent or a combination thereof, wherein the organic solvent is selected from the group consisting of halogenated hydrocarbons, ethers, esters, amides and alcohols, to give a compound of the formula (I):

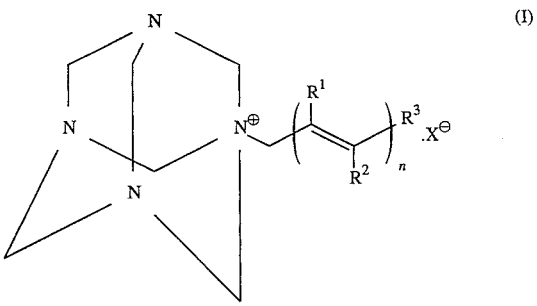

wherein each symbol is as defined above and a compound of the formula (II):

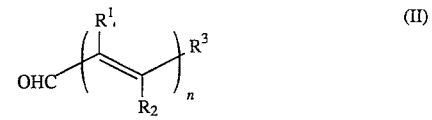

wherein each symbol is as defined above; followed by, if necessary, adding water or organic solvent as defined above to the reaction mixture, and then separating the resultant mixture into aqueous and organic layers, and i) subjecting the resultant compound of the formula (I) in the aqueous layer to hydrolysis in the presence of an organic solvent homogenously immiscible with water wherein the organic solvent is selected from the group consisting of halogenated hydrocarbons, ethers and esters, while ii) reacting the resultant compound of the formula (II) in the organic solvent as defined above with sodium hydrogensulfite to give a compound of the formula (III):

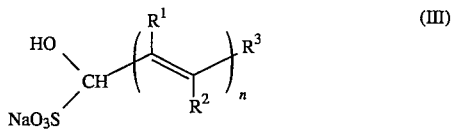

wherein each symbol is as defined above, and iii) reacting the resultant compound of the formula (III) with formaldehyde in water and an organic solvent homogenously immiscible with water and the organic solvent as defined above.

13. A process according to claim 12, wherein the hydrocarbon group of the unsubstituted or substituted hydrocarbon group represented by $R^3$ is a straight-chain or branched alkyl group having 1 to 6 carbon atoms.

14. A process according to claim 12, wherein the substituent of the substituted hydrocarbon group represented by $R^3$ is $C_{1-4}$ alkoxy group, $C_{1-10}$ acyloxy group, $C_{1-5}$ alkoxycarbonyl group, cyano group, oxo group or group of the formula:

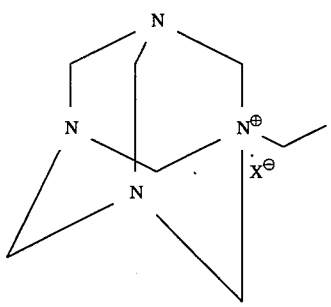

wherein X is halogen.

15. A process according to claim 12, wherein the substituent of the substituted hydrocarbon group represented by $R^3$ is an acyloxy group having 1 to 10 carbon atoms.

16. A process according to claim 12, wherein n is an integer of 1 to 5.

17. A process according to claim 12, wherein $R^1$ is a methyl group, $R^2$ is hydrogen, $R^3$ is an acetoxymethyl group, and n is 1.

18. A process according to claim 12, wherein the compound of the formula (I) in the aqueous layer is subjected to hydrolysis in the presence of an organic solvent immiscible with water, and the amount of the organic solvent is about 1 to about 3 times (v/v) that of the water.

19. A process according to claim 12, wherein the compound of the formula (I) in the aqueous layer is subjected to hydrolysis in the presence of an organic solvent immiscible with water, an the amount of the water is about 0.5 to about 2 liters per mol of the compound of the formula (I).

20. A process according to claim 12, wherein the compound of the formula (I) in the aqueous layer is subjected to hydrolysis in the presence of an organic solvent immiscible with water, and the hydrolysis is carried out at a pH of about 4 to about 7.

21. A process according to claim 12, wherein the compound of the formula (I) in the aqueous layer is subjected to hydrolysis in the presence of an organic solvent immiscible with water, and the organic solvent is selected from hydrocarbons, halogenated hydrocarbons and ethers.

22. A process according to claim 12, wherein the compound of the formula (I) in the aqueous layer is subjected to hydrolysis in the presence of an organic solvent immiscible with water, and the hydrolysis is carried out at about 60° to about 80° C.

23. A process according to claim 12, wherein the amount of the sodium hydrogensulfite is about 1 to about 2 mol per mol of the compound of the formula (II).

24. A process according to claim 12, wherein the amount of the formaldehyde is about 1 to about 2 mol per mol of the compound of the formula (II).

25. A method of purifying a compound of the formula (II):

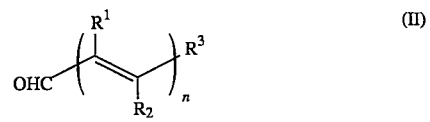

wherein $R^1$ and $R^2$ are each hydrogen or a straight-chain or branched alkyl group having 1 to 6 carbon atoms, $R^3$ is hydrogen or an unsubstituted or substituted hydrocarbon group having 1 to 20 carbon atoms, and n is an integer of 1 to 10, which comprises reacting a compound of the formula (II) with sodium hydrogensulfite to give the compound of the formula (III):

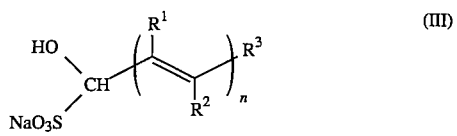

wherein each symbol is as defined above, and reacting the compound of the formula (III) with formaldehyde in water and an organic solvent homogenously immiscible with water, wherein the organic solvent is selected from the group consisting of halogenated hydrocarbons, ethers and esters.

26. A method according to claim 25, wherein the hydrocarbon group of the unsubstituted or substituted hydrocarbon group represented by $R^3$ is a straight-chain or branched alkyl group having 1 to 6 carbon atoms.

27. A method according to claim 25, wherein the substituent of the substituted hydrocarbon group represented by $R^3$ is $C_{1-4}$ alkoxy group, $C_{1-10}$ acyloxy group, $C_{1-5}$ alkoxycarbonyl group, cyano group, oxo group or group of the formula:

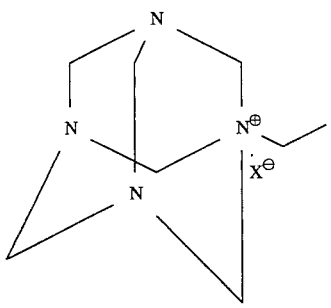

wherein X is halogen.

28. A method according to claim 25, wherein the substituent of the substituted hydrocarbon group represented by R³ is an acyloxy group having 1 to 10 carbon atoms.

29. A method according to claim 25, wherein n is an integer of 1 to 5.

30. A method according to claim 25, wherein $R^1$ is a methyl group, $R^2$ is hydrogen, $R^3$ is an acetoxymethyl group, and n is 1.

31. A method according to claim 25, wherein the amount of the sodium hydrogensulfite is about 1 to about 2 mol per mol of the compound of the formula (II).

32. A method according to claim 25, wherein the amount of the formaldehyde is about 1 to about 2 mol per mol of the compound of the formula (II).

* * * * *